US006402947B1

(12) United States Patent
Altamirano et al.

(10) Patent No.: US 6,402,947 B1
(45) Date of Patent: Jun. 11, 2002

(54) INTERPHASE DEVICE FOR THE DIRECT COUPLING OF LIQUID CHROMATOGRAPHY AND GAS CHROMATOGRAPHY

(75) Inventors: Jesús Villen Altamirano, Ciudad Real; M$^a$ Luisa Marina Alegre, Alcalá de Henares; Marta Herraiz Carasa, Madrid; Graciela Patricia Blanch Manzano, Madrid; Ana Maria Vázquez Molini, Madrid, all of (ES)

(73) Assignees: Consejo Superior de Investigaciones Cientificas, Madrid; Universidad de Castilla-La Mancha, Ciudad Real; Universidad de Alcala de Henares, Alcala de Henares, all of (ES)

( * ) Notice: Subject to any disclaimer, the term of this patent is extended or adjusted under 35 U.S.C. 154(b) by 0 days.

(21) Appl. No.: 09/700,985
(22) PCT Filed: May 14, 1999
(86) PCT No.: PCT/ES99/00137
§ 371 (c)(1),
(2), (4) Date: Mar. 9, 2001
(87) PCT Pub. No.: WO99/61127
PCT Pub. Date: Dec. 2, 1999

(30) Foreign Application Priority Data

May 22, 1998 (ES) ............................................. P9801068

(51) Int. Cl.$^7$ ............................................. B01D 15/08
(52) U.S. Cl. .................... 210/198.2; 210/656; 210/659; 96/101; 96/103; 96/104; 422/70
(58) Field of Search ................................ 210/634, 635, 210/656, 659, 198.2; 96/101, 103, 104; 422/70

(56) References Cited

U.S. PATENT DOCUMENTS

| 4,766,760 A | 8/1988 | Poshemanski et al. ....... 73/23.1 |
| 5,139,681 A | * 8/1992 | Cortes ......................... 210/659 |

(List continued on next page.)

FOREIGN PATENT DOCUMENTS

| WO | WO 92/05851 | 4/1992 | .............. 210/198.2 |

OTHER PUBLICATIONS

Mondello, L. et al, J. Microcolumn Separations, 8(4) 275–310; 1996.
Vreuls, J.J. et al, Journal Of AOAC International, vol. 77, No. 2, 306–327; 1994.
Senorans, F.J. et al, J. Agric. Food Chem, vol. 46, No. 3, 1022–1026; 1998.

(List continued on next page.)

Primary Examiner—Ernest G. Therkorn
(74) Attorney, Agent, or Firm—Klauber & Jackson

(57) ABSTRACT

The basic structure of a PTV (programmed temperature vaporizer) injector has been considerably modified so that is can be used for the direct coupling of liquid chromatography in normal phase or reverse phase, and gas chromatography and also for the introduction of high volumes in gas chromatography. The glass tube of the injector is filled with an adsorbent. By means of a system of valves and tubes or capillary tubes, the previously selected fraction of liquid chromatography is transferred to the injector, said fraction coming in through the same extremity for introducing the gas chromatography column. The eluent is entrained by a gas stream through the adsorbent, wherein are retained the solutes, and the solvent is removed through a tube or capillary tube introduced in the injector through the opposite extremity. Thereafter, the solutes are desorbed thermally passing to the chromatography column.

12 Claims, 5 Drawing Sheets

U.S. PATENT DOCUMENTS

| | | | |
|---|---|---|---|
| 5,180,487 A | | 1/1993 | Saito et al. .............. 210/198.2 |
| 5,234,599 A | * | 8/1993 | Cortes ....................... 210/659 |
| 5,340,475 A | * | 8/1994 | Cortes ..................... 210/198.2 |
| 5,376,277 A | * | 12/1994 | Cortes ....................... 210/659 |
| 5,522,988 A | * | 6/1996 | Cortes ..................... 210/198.2 |

OTHER PUBLICATIONS

Grob, K., Journal of Chromatography A, 703, 265–276; 1995.

Villen, J. et al, J. Agric. Food Chem., vol. 46, No. 4, 1419–1422; 1998.

* cited by examiner

INTERPHASE DEVICE FOR THE DIRECT COUPLING OF LIQUID CHROMATOGRAPHY AND GAS CHROMATOGRAPHY

REFERENCE TO RELATED APPLICATIONS

This application is a 371 of PCT/ES99/00137 filed May, 14, 1999.

PRIOR ART

The use of a direct coupling of high efficiency liquid chromatography and gas chromatography is very useful for analyzing complex mixtures. The advantages in using this multidimensional system basically centre on the possibility of combining the liquid chromatography potential as a sample preparation technique with that of gas chromatography in relation to the system's efficiency (Grob. K., *On-Line Coupled LC-GC.*, Hüthig, Heidelberg, Germany, 1991; Mondello, L.,; Dugo, G.; Bartle, K. D., *J. Microcol,* Sep., 1996, 8, 275–310). In this way, it is possible to avail of analysis methods which do not require the use of conventional sample preparation procedures which, apart from being laborious and unreliable, have the great disadvantage of calling for the use of relatively high volumes of polluting organic solvents.

A particularly problematic aspect in connection with the use of direct coupling of liquid chromatography and gas chromatography relates to the characteristics of the interface necessary to make this coupling possible. This is an aspect which displays the difficulty in making two essentially different systems, where the operating parameters are substantially different, compatible. The interfaces initially developed only allowed the use of a normal phase in the pre-separation performed by liquids since, in this case, the small volumes of vaporization produced during the transfer do not lead to any additional difficulties. This is why different interfaces ("autosampler", "on-column", "loop type") enabling direct coupling to be carried out between liquid chromatography in the normal phase and gas chromatography (Grob, K. J. *Chromatogr. A* 1995, 703, 265–76; Vreuls, J. J.,; de Jong, G. J.; Ghijsen, R. T.; Brinkman, U. A. Th. *J. AOAC. Int* 1994, 77, 306–27) have been designed and used.

However, it is necessary in many cases to turn up to the use of the reverse phase in the liquid chromatography stage in order to achieve a certain separation and, consequently, the extension of the field of applicability of direct liquid chromatography and gas chromatography coupling requires the development of suitable interfaces for carrying out direct coupling between liquid chromatography in a reverse phase and gas chromatography (Señoráns, F. J.,; Villén, J; Tabera, J.; Herraiz, M. J. *Agric. Food Chem.* 1998, 46, 1022–27. Villén, J; Blanch, G. P.; Ruiz del Castillo, M. L.; Herraiz, M. *J. Agric. Food Chem.* 1998, 46, 1027–31. With this aim in mind, several systems have been proposed over the last few years ("retention gap", "concurrent solvent evaporation", "open tubular trap", etc.) (Grob, K. *J. Chromatogr. A* 1995, 703, 265–76; Vreuls, J. J.; de Jong, G. J.; Ghijsen, R. T.; Brinkman, U. A. Th., *J. AOAC. Int.* 1994, 77, 306–27) although the limitations involved in using polar eluents (fundamentally the high volumes of vaporization produced during transfer and the difficulty of suitably focussing the chromatographic band) have prevented the development of interfaces meeting the required conditions as regards simplicity, reliability, versatility and possibility of automation.

Interfaces described up to date in literature have limitations in some of the following aspects: The liquid chromatography fraction's volume that can be transferred, the flow rate at which this fraction can be transferred, the impossibility of making the transfer when liquid chromatography is performed in the reverse phase, or the system cannot be automated.

The liquid chromatography fraction volume normally transferred with the systems described is about 500 microliters and rarely exceeds one milliliter and then only by a little. This makes it necessary to transfer only a part of the liquid chromatography fraction of interest or leads to working with very small diameter columns in liquid chromatography (liquid microchromatography), which means experimental difficulties and a loss of sensitivity. Some interface allowing much greater volumes to be transferred has been described, but it cannot be automated. In the device which is the subject of the invention, the volume of the fraction transferred is unlimited. Up to 100 ml have been inserted, a much higher volume than any liquid chromatography fraction it is desired to transfer with analytical ends, but this volume can be far exceeded when required.

The flow rate at which the transfer is performed is limited by the solvent evaporation rate in most of the systems described. This also makes it necessary to work in liquid microchromatography or to use an interface having a system which collects the liquid chromatography fraction and transfers it to gas chromatography at a lower flow rate at which it elutes from liquid chromatography, and this increases the complexity of the interface. Some interface has been described which allows transfer to be made at a much greater flow rate than the rest, but it cannot be automated. In the device which is the subject of the invention, the flow rate at which the liquid chromatography fraction is transferred is far higher than any of the systems described which may be automated. Transfers have been made at 5 milliliters per minute, a far higher rate than that necessary to transfer a liquid chromatography fraction with analytical ends, but this rate may be far exceeded if required.

Most of the interfaces described only allow the transfer to be made when liquid chromatography is performed in a normal phase. This means a limitation in itself, which is substantial if it is borne in mind that the immense majority of liquid chromatography separations have been carried out in the reverse phase. The interfaces described which allow liquid chromatography fractions to be transferred in the reverse phase make a change in solvent during the transfer or cannot be automated or have the limitations as discussed earlier. In the device which is the subject of this invention, liquid chromatography can be performed both in the normal and in reverse phases. It also allows very high volumes of aqueous solution to be transferred at a high flow rate.

The difficulty in achieving direct coupling of liquid chromatography and gas chromatography lies in the fact that the maximum volume of sample that can be inserted into a gas chromatography capillary column is in the order of one microliter, whilst a liquid chromatography fraction of interest normally has a volume between about 100 microliters and a few milliliters. Therefore, the interface employed for this direct coupling has to evaporate the solvent to the volume admissible in gas chromatography, retain the solutes of interest and transfer them to the gas chromatography column occupying a narrow band of the column, so that chromatographic separation is effective.

An increase of analysis sensitivity is achieved by introducing high volumes of sample or extract in gas chromatography. Due to this increase in sensitivity, the extraction and concentration processes prior to the gas chromatography analysis may be replaced in many cases by introducing high volumes of sample. The difficulty with this technique is basically the same as that of liquid chromatography and gas chromatography coupling, i.e. to evaporate the solvent from the high volume inserted until the solution has a volume lower than the maximum admissible by the gas chromatography capillary column, retain the solutes and move them into the gas chromatography column.

Therefore, if there is no specific instrumental difficulty, any device suited for using as an interface for direct liquid chromatography and gas chromatography coupling is also suited to the introduction of high volumes of sample in gas chromatography, and vice-versa.

DESCRIPTION OF THE INVENTION

The device according to the present invention is built on the basis of the scheme of a PTV (programmed temperature vaporizer) injector in which the system for inserting the sample, the hydraulic gas system and the operating mode have been modified. Thus, the present invention provides an interface device for direct coupling of liquid chromatography and gas chromatography based on a programmed temperature vaporizer (PTV), the device being capable of operating at least in an adsorption mode and in a desorption mode, and comprising

- an injector divided into a first inner part and a second inner part and which houses a glass liner containing an adsorbent, the glass liner having a first end portion within the first inner part and a second end portion within the second inner part of the injector;
- a system for selecting a liquid chromatography fraction and conducting the liquid chromatography fraction to the glass liner, said system comprising a first tube protruding into the glass liner and a first valve connected to a second end of the first tube;
- a discharge system for discharging the liquid chromatography fraction into the glass liner and for preventing, when the device operates in the adsorption mode, the liquid chromatography fraction from entering a gas chromatography column, the discharge system comprising
  - a first end of the first tube terminating within the glass liner at a first distance from the adsorbent, the gas chromatography column having an inlet protruding into the glass liner by said first end portion, said inlet being located within the glass liner at a second distance from the adsorbent, said first distance being shorter than said second distance,
  - a first gas inlet for entry of a pressurized gas flow into said first inner part of the injector,
  - a second gas inlet for entry of pressurized gas into said second inner part of the injector, and
  - a second tube protruding into the glass liner by said second end portion;
- an outlet system for evacuating solvent from the glass liner, the outlet system comprising an outlet valve connected within the second tube, the outlet valve being closed in the desorption mode and open in the adsorption mode; and
- a modified hydraulic system for gases connected to the first gas inlet and to the second gas inlet and to a gas tank containing pressurized gas for providing the pressurized gas flow.

The operation of the device during the transfer of the liquid chromatography fraction of interest, is based on two principles: adsorption in the solid phase and solvent evaporation. The thermal desorption of the solutes retained takes place subsequently.

The glass liner of the PTV injector is filled with an adsorbent. The inlet end of the capillary chromatographic column is inserted into the injector in the usual way. The first end of the first tube is also inserted at the same place up to the glass liner. It will carry the fraction from liquid chromatography down to a depth deeper than the inlet end of the gas chromatography column. This first tube is connected at the end opposite to the liquid chromatograph through a system of valves allowing the liquid chromatography fraction of interest to be selected, and the eluent remaining in the transfer tube or capillary when the transfer has finished to be removed.

The second tube protrudes outside the injector and takes the solvent removed to a waste, and can have an opening and closing valve and an intermediate opening and closing valve, and it is inserted through the opposite end of the glass liner.

The hydraulic gas chromatograph system is modified by a system of pressure reducers, opening and closing valves and flow controlling valves so that it is allowed to operate in two modes, adsorption or desorption.

Controlled flows of gas may be sent in through both ends of the glass liner in the adsorption mode. This mode is used during the transfer and subsequent disposal of solvent remains. The gas entering the glass liner through the same place as the first tube pushes the liquid towards the adsorbent and draws the solvent along to the second tube. The gas entering the glass liner through the opposite end prevents the injector from being flooded.

In the desorption mode, gas only reaches the glass liner through the inlet used in the usual configurations, at a controlled pressure. The thermally desorbed solutes are taken by this flow of gas to the capillary column where the chromatographic process takes place.

As readily apparent, contrary to prior art interfaces, the devices which is the objet of the present invention allows a very large volume liquid chromatography fraction to be transferred (or directly injected) at a very high flow rate, allows liquid chromatography fractions in a normal phase or reverse phase to be transferred and can be automated. It also allows large volumes of sample or extract to be directly inserted, both with polar and non-polar solvents.

BRIEF DESCRIPTION OF THE DRAWINGS

The invention will hereinafter further described on the basis of several drawings in which.

DETAILED DESCRIPTION OF THE INVENTION

Figure 1:
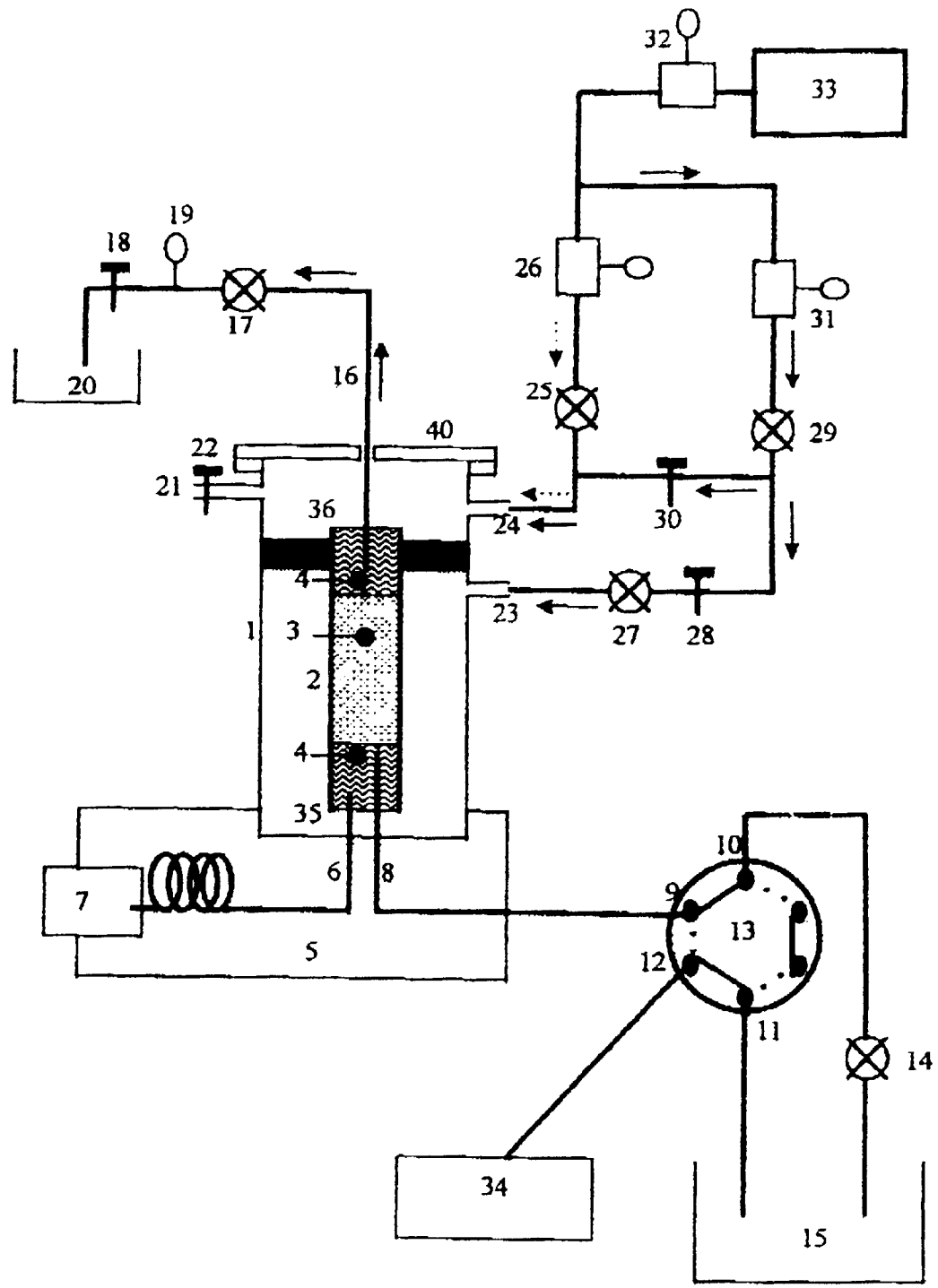
FIG. 1 is a schematical view showing the device of the present invention

According to FIG. 1, the device is built on the basis of the scheme of a PTV (programmed temperature vaporizer)

injector 1 in which the sample inserting system, the hydraulic gas system and the operating mode have been modified.

The glass liner 2 of the PTV injector is filled with an adsorbent 3 placed between securing means 4 so that the adsorbent 3 is prevented from moving.

The inlet of the gas chromatography chromatographic capillary column 6 is connected to the PTV injector 1 in the usual manner and its end is therefore fitted inside the glass liner 2, into which it has been inserted at the part nearest to the oven 5 of the gas chromatograph (hereinafter referred to as the first part 35). Another tube 8 is inserted at the same place. This first tube 8 will carry a fraction from liquid chromatography so that the portion of this first tube 8 inserted within the glass liner 2 is longer than the portion of the gas chromatography column 6 which is also inside the glass liner 2.

The first tube 8 is connected at the opposite end to way 9 of a first valve 13. The ways referenced 10 and 11 in FIG. 1 lead the liquid to waste 15. The tube or capillary which connects way 10 to waste 15 has an intermediate opening and closing, second valve 14. Way 12 is connected to the liquid chromatograph 34.

When it is intended to use the device for inserting high volumes of sample or extract in gas chromatography, the liquid chromatograph 34 is replaced by a sample or extract driving system.

A further tube 16 (hereinafter to as second tube) is inserted by the end of the glass liner 2 which is farthest away from the gas chromatography oven 5 i.e. by the first end of the glass liner 2 located within the second inner part 36 of the injector 1, said second tube protruding from the injector 1 at the point where a syringe is inserted in normal operation. This second tube 16 leads to waste 20. An opening and closing outlet valve 17 and a flow regulator 18 which may be inserted before or after the outlet valve 17, are fitted between the injector 1 and waste 20. The flow regulator 18 may be replaced by a pressure regulator.

The hydraulic gas chromatograph system is modified. It contains three pressure reducers, three opening and closing gas valves and two flow regulators arranged as shown in FIG. 1. This hydraulic system allows operation in two different modes, which we call adsorption and desorption.

In the adsorption mode, gas valve 25 is closed and gas valves 27 and 29 are open. By using regulators 28 and 30, controlled flows of gas may be sent through the second end of the glass liner 2 located within the injector 1 nearest to the chromatography oven 5, through the second gas inlet 24 for the carrier gas to the injector 1 and, simultaneously, through the first end of the glass liner 2 through the first gas inlet 23 which, in the injector's classical operating mode, is used as a flow division outlet.

In the desorption mode, valve 25 is open and valves 27 and 29 are closed, so the glass liner 2 only receives helium through the second inner part 36, at a pressure controlled by the pressure reducer 26.

All opening and closing valves included in the device, as well as valve 13 which preferably has at least four ways, may be hand operated or electrically controlled (normally called in the latter case electrovalves or electric actuators or pneumatic actuators). Moreover, most of the liquid chromatography and gas chromatography units currently being marketed are equipped with several electrical outputs to control this type of valve from the unit so that its opening and closing or operation in the case of a several way valve may be programmed in time through the programming system these units avail of to control several parameters of the chromatography equipment. Therefore, the device which is the subject of the invention may operate manually or automatically. In addition, if the liquid chromatograph has an automatic injector, the unit composed of the liquid chromatograph, the interface device and the gas chromatography may operate repeatedly coupled in a totally automatic fashion.

Operating Mode of the Device

Four stages may be differentiated:
1) Stabilization.

Figure 2:
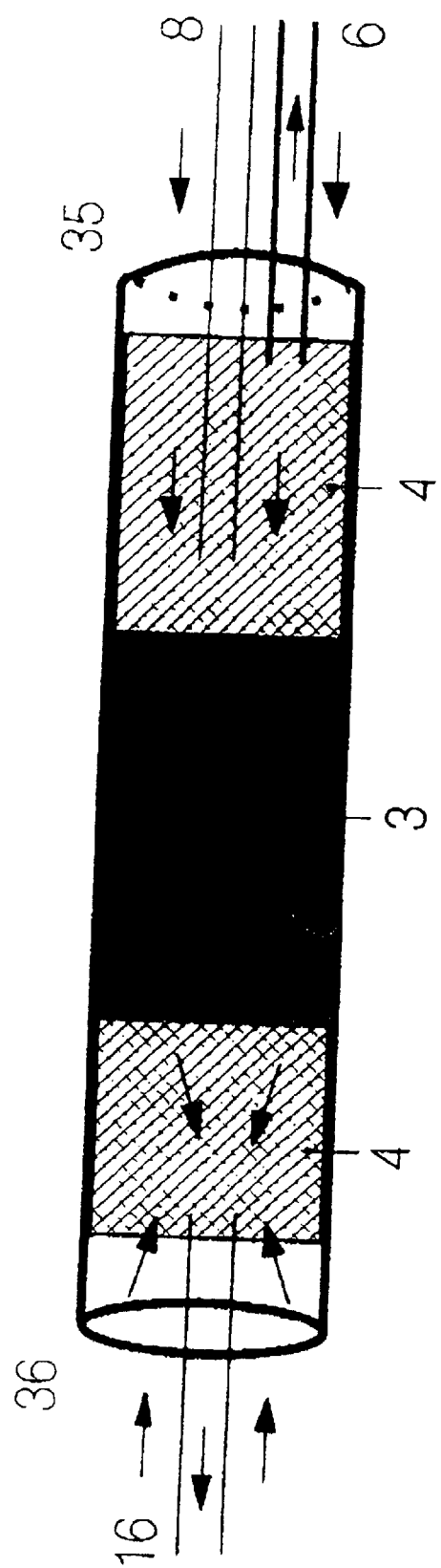
FIG. 2 is a partial schematic view of the device shown in FIG. 1 when operating in a stabilization mode

Before commencing transfer, the temperature at which this will be performed is stabilized and must be that suitable for the solutes to be adsorbed in the adsorbent and the solvent to be removed. During this time, gas circulates through the glass liner 2 in the adsorption mode described earlier, as shown in FIG. 2. Helium entering the glass liner 2 exits through the second tube 16, for which purpose valve 17 is open. The flow regulator 18, or the pressure controller by which this valve may be replaced, regulates the pressure inside the glass liner. Valve 13 is then in the position shown with a continuous line in FIG. 1, whereby the liquid chromatography eluent is sent to waste. Valve 14 is closed in this phase.

2) Transfer

Figure 3:
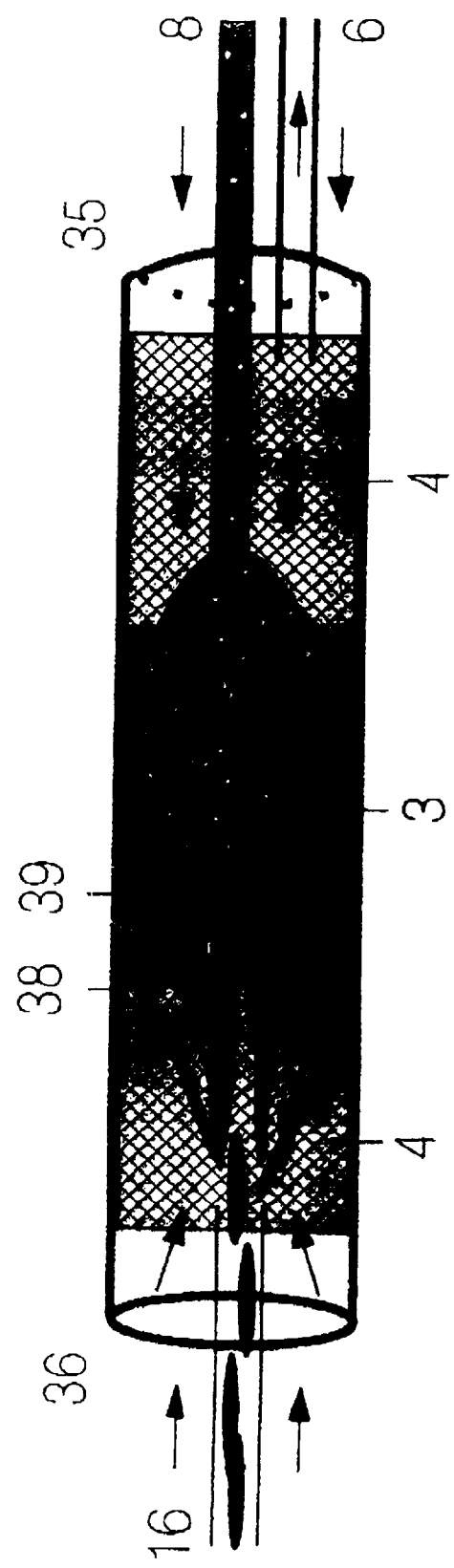
FIG. 3 is a partial schematic view of the device shown in FIG. 2 when operating in a transfer mode

When the fraction of interest is eluted from the liquid chromatograph 34, valve 13 is operated and remains in the position as indicated with a broken line in FIG. 1, whereby the eluent is transferred to the glass liner 2 through the first tube 8. The flow of gas entering through the first inner part 35 pushes the eluent 37 through the adsorbent 3 (FIG. 3) in which the analytes are retained. As the gas chromatography column 6 has been inserted into the glass liner to a depth less than that of the first tube 8, the eluent moves away from column 6, so that the eluent is prevented from entering column 6. This flow of helium also produces partial or total evaporation of the solvent 38. The totally or partially evaporated solvent is removed by the second tube 16. The flow of gas entering through the second end of the glass liner 2 prevents the solvent overpassing it, thereby avoiding that the area of the injector between the second end of the glass liner 2 and the outside closure 40 of the injector becomes flooded.

3) Removal of solvent remains

Figure 4:
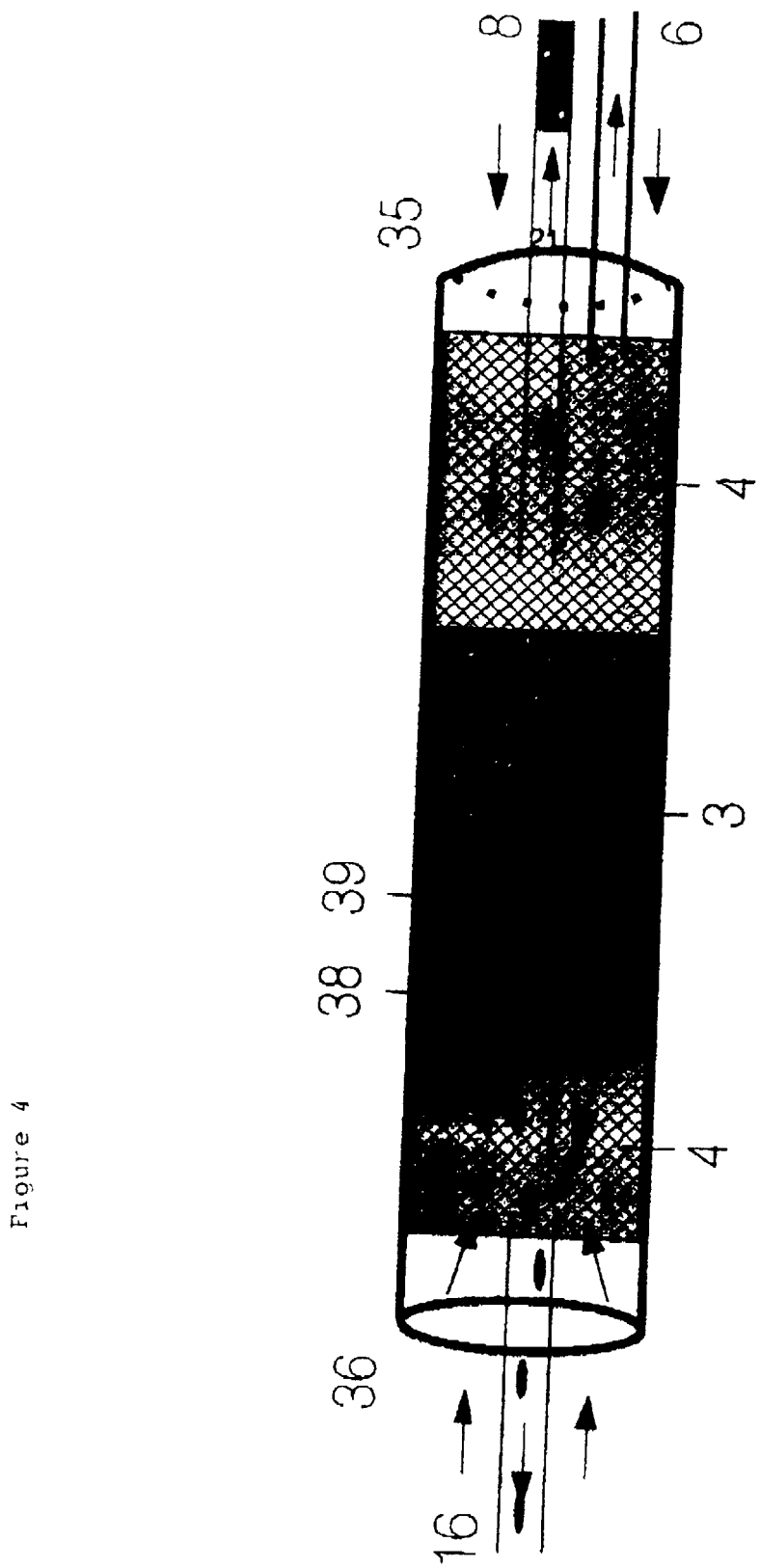
FIG. 4 is a partial schematic view of the device shown in FIG. 2 when operating in a mode of removal of solvent remains

When elution of the fraction of interest has finished, valve 13 is activated and remains in the position as shown in the continuous line in FIG. 1, whereby the liquid chromatography eluent is sent to waste. At the same time, valve 14 is opened so that the helium under pressure inside the injector pushes the liquid chromatography eluent which has remained in the first tube 8 between valve 13 and the glass liner 2 to waste 15, thus preventing possible problems of contamination in the next analysis (FIG. 4).

The device is then left under these conditions for the time required for drying. The gas which continues passing through the injector during this time removes the solvent remains and only the compounds retained by the adsorbent remain inside the glass liner (FIG. 4).

4) Thermal desorption

Figure 5:
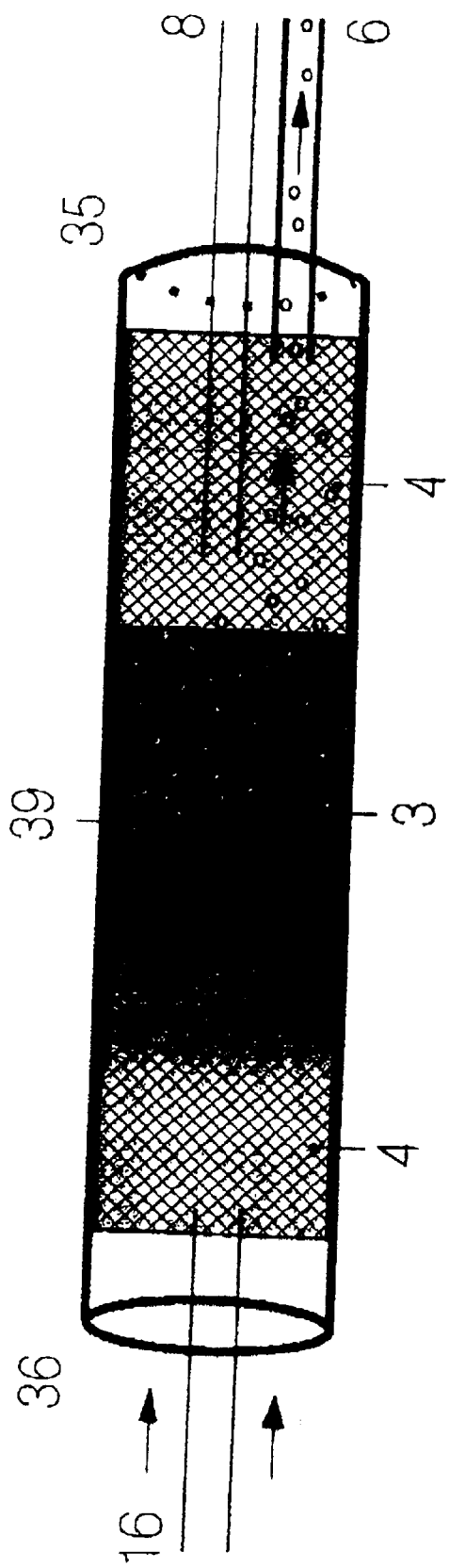
FIG. 5 is a partial schematic view of the device shown in FIG. 2 when operating in a thermal desorption mode.

Once the time for solvent removal has ended, valves 14, 17, 27 and 29 are closed (FIG. 1) and valve 25 is opened. The gas thus enters the glass tube 2 only through the second end (cf. desorption mode explained earlier) and exits through column 6 (FIG. 5). At that time, the injector 1 is swiftly heated to the temperature necessary to produce thermal desorption of solutes 39, which are drawn along by the gas to column 6 and the chromatographic process commences.

When it is intended to use the device to introduce large volumes of sample or extract in gas chromatography, the operating mode is almost the same but differentiated in that by opening and closing valve 13, the time the sample or extract is moving towards the glass liner 2 is controlled. Knowing the flow rate at which the driving system is supplying liquid, the sample or extract volume which has been introducer into glass liner 2 and, thereby, into the gas chromatography column 6, can be controlled.

EXAMPLE OF AN EMBODIMENT OF THE INVENTION

A Varian 3400 gas chromatograph was used, fitted with a PTV injector (called by the maker "PSS injector") and a thermionic detector in which a capillary column of 0.32 millimeters internal diameter and 30 meters length was fitted.

The liquid chromatograph is made up of an isocratic pump (Hewlett Packard), a U6K Injector (Waters), a column and a fixed wave length ultra-violet detector (Waters).

The PTV injector's glass liner 2 is 53 mm long, and has a 4.5 mm outside and 2 mm inside diameter. It is filled with 2 cm of an adsorbent 3, Tenax TA 80–100 mesh, secured by two pieces of glass wool 4 so as to prevent the adsorbent from moving.

The capillary chromatographic column 6 is placed so that it is 5 mm deep in the glass liner 2. The inside tube or capillary i.e. the first tube 8, which will carry the fraction from liquid chromatography, is a 0.32 mm inside diameter capillary which is inserted down to 15 mm depth in the glass liner. A rapid connector (Chrompack) with a graphite cone with two 0.5 mm orifices was used to insert the two capillaries 6 and 8.

This inside capillary 8 is connected to way 9 of a 6 way valve (valve 13 in FIG. 1). Ways 10 and 11 lead the liquid to waste via a 1/16" (=0.15875 cm) stainless steel pipe. The connection between way 10 and waste has an intermediate opening and closing valve 14. Way 12 is connected to the liquid chromatograph detector's outlet.

The second tube 16 has 0.32 mm of internal diameter and is 20 cm long. It is inserted 10 mm down into the glass liner. It comes out of the injector through the septum, leading to waste with an intermediate opening and closing valve 17. The flow or pressure regulator 18 and pressure gauge 19 are not necessary in this example because the capillary 16 acts as a restrictor.

The hydraulic gas system is built on the basis of the diagram in FIG. 1 in which the toggle type closing and opening valves 25, 27 and 29, flow regulators 28 and 30 are hand operated needle valves, and the pressure reducers are also hand operated. The tubes used for the connections are 1/8" (=0.3175 cm) copper. Helium contained in a bottle is used as gas 33.

The pressure reducer 31 is regulated to 6 Kg/cm$^2$. The needle valve 28 is regulated so that helium flows at 2500 ml/min and will enter the glass liner 2 through the inside. Needle valve 30 is regulated so that helium flows at 1000 ml/min and will enter glass tube 2 through its second end.

Pressure reducer 26 is regulated at a pressure of 1.2 Kg/cm$^2$

An analysis of a solution of the following water organo-phosphorated pesticides was applied: Fenitrotion, fention, paration fentoate, fenamifos, etion and gution (by order of elution in gas chromatography). The pesticides mentioned were separated under these conditions from other impurities in the sample in the liquid chromatography. The fraction of interest which was transferred to gas chromatography and contained the pesticides had a volume of 1 milliliter. The transfer was made as per the operating mode indicated earlier with a 1 ml/min flow rate. The temperature at which the PTV injector stabilized and at which it was kept until the solvent remains were removed, was 10° C. Thermal desorption of the pesticides retained in the adsorbent was performed by heating the injector to 250° C. The concentration of pesticides in the initial aqueous solution was quantified through the chromatogram obtained by gas chromatography.

DETAILED DESCRIPTION OF THE OF THE NUMMERICAL REFERENCES IN THE DRAWINGS

1: PTV injector
2: glass liner
3: Adsorbent with which glass tube 2 was filled
4: Adsorbent securing means which may be glass wool
5: Gas chromatography oven
6: Gas chromatography column
7: Gas chromatograph detector
8: First tube leading the liquid chromatography fraction of interest to the glass liner
9, 10, 11 and 12: Ways of a four or more way valve.
13: Four or more way valve; the valve represented in FIG. 1 is a six way and two position valve. The position shown by continuous lines is that it should adopt when the liquid chromatograph eluent is not of interest and is therefore sent to waste. The position shown by broken lines is that the valve should adopt when the liquid chromatograph eluent corresponds to the fraction of interest and is therefore to be transferred to the gas chromatograph.
14: First opening and closing valve. When open, this valve allows the eluent which has remained in the first tube 8 to exit to waste when valve 13 changes position when the transfer terminates, pushed by the gas under pressure inside the glass liner 2. When closed, the glass liner 2 is isolated from the outside by this connection.
15: Wast
16: Second tube through which the gas in the glass liner exits, as well as the totally or partially evaporated solvent drawn along by the gas.
17: Second opening and closing valve. When open, it allows the gas and solvent to exit to waste when the fraction of interest is being transferred and during the subsequent phase where solvent remains are disposed of. When this valve is closed, the glass liner 2 is isolated from the outside by this connection.
18: Flow regulator valve, which may be replaced by a pressure reducer
19: Pressure gauge
20: Waste
21: Injector septum bleed outlet
22: Septum bleed flow regulator valve
23: First gas inlet which is an injector connection to the outside which would be used as a flow division outlet in the normal operating mode
24: Second gas inlet which would be gas entry in normal operating mode.
25: Opening and closing valve. This first gas valve is open in the desorption mode, allowing gas to pass to the injector to draw along the thermally desorbed solutes to the gas chromatography column and to act as a moving phase. This valve is closed in the adsorption mode.
26: Pressure reducer regulating the pressure at which the gas enters the injector through valve 25 and inlet 24

27: Opening and closing valve. This third gas valve is open in the adsorption mode, allowing gas to enter the injector through inlet 23. This gas penetrates into the glass liner 2 through its first end, drawing along the liquid chromatography eluent to the adsorbent 3 and the solvent to the second tube 16. This valve is closed in the desorption mode.

28: Regulator valve for flow through valve 27

29: Opening and closing valve. This second gas valve is open in the adsorption mode, allowing gas to enter the injector simultaneously through inlets 23 and 24. This valve is closed in the desorption mode.

30: Regulator valve for flow entering the injector through inlet 24. The gas prevents the solvent from exceeding the point in the glass tube 2 where the outside capillary 16 has been placed, thus preventing the solvent from deposited in the part of the injector through which this gas flow passes.

31: Pressure reducer which regulates the pressure of the gas flowing in the desorption mode 32: Pressure reducer which regulates the general gas pressure in the whole system 33: Gas tank 34: Liquid chromatograph. When it is intended to use the device described for introducing high sample or extract volumes in gas chromatography, the liquid chromatograph must be replaced by an extract or sample driving system.

35: Part of the injector nearest the gas chromatograph oven (=first inner part)

36: Part of the injector farthest from the gas chromatograph oven (=second inner part)

37: Liquid chromatography eluent (either sample or extract)

38: Solvent

39: Solutes

40: Outside injector lock

In the figures, continuous line arrows show the direction of gas flow in the adsorption mode and broken line arrows the flow direction in the desorption mode.

What is claimed is:

1. An interface device for direct coupling of liquid chromatography and gas chromatography based on a programmed temperature vaporizer (PTV), the device being capable of operating at least in an adsorption mode and in a desorption mode, and comprising
    an injector (1) divided into a first inner part (35) and a second inner part (36) and which houses a glass liner (2) containing an adsorbent (3), the glass liner (2) having a first end portion within the first inner part (35) and a second end portion within the second inner part (36) of the injector (1);
    a system for selecting a liquid chromatography fraction and conducting a liquid chromatography fraction to the glass liner (2), said system comprising a first tube (8) protruding into the glass liner (2) and a first valve (13) connected to a second end of the first tube (8);
    a discharge system for discharging the liquid chromatography fraction into the glass liner (2) and for preventing, when the device operates in the adsorption mode, the liquid chromatography fraction from entering a gas chromatography column (6), the discharge system comprising
        a first end of the first tube (8) terminating within the glass liner (2) at a first distance from the adsorbent (3), the gas chromatography column (6) having an inlet protruding into the glass liner (2) by said first end portion, said inlet being located within the glass liner (2) at a second distance from the adsorbent (3), said first distance being shorter than said second distance,
        a first gas inlet (23) for entry of a pressurized gas flow into said first inner part (35) of the injector (1),
        a second tube (16) protruding into the glass liner (2) by said second end portion;
    an outlet system for evacuating solvent from the glass liner (2), the outlet system comprising an outlet valve (17) connected within the second tube (16), the outlet valve (17) being closed in the desorption mode and open in the adsorption mode; and
    a hydraulic system for gases comprising a system of pressure reducers, opening and closing valves, and flow controlling valves, connected to the first gas inlet (23) and to the second gas inlet (24) and to a gas tank (33) containing pressurized gas for providing the pressurized gas flow.

2. A device according to claim 1, wherein the first valve (13) has at least four ways (9,10,11,12), whereby a first way (9) is connected to the first tube (8), a second way (10) and a third way (11) lead to a waste (15), and a fourth way (12) leads to a liquid chromatograph (34), to an extract impelling system or to a sample impelling system, the first way (9) alternatively being open towards the second way (10) or to the fourth way (12), the fourth way (12) when not connected with the first way (9), being connected with the waste (15) through the third way (11), the second way (10), when connected with the first way (9), being also connected with the waste (15) through a second valve (14), whereby, when the device operates in the adsorption mode, the first way (9) is open towards the fourth way (12) and closed towards the second way (10) whilst, when the device operates in the desorption mode, the first way (9) is closed towards the fourth way (12) and open towards the second way (10).

3. A device according to claim 1, wherein, in the hydraulic system for gases, the gas tank (33) is connected to the first gas inlet (23) and to the second gas inlet (24) through
    a first gas valve (25) connected between the gas tank (33) and the second gas inlet (24), the first gas valve (25) being closed when the device operates in the adsorption mode and open when the device operates in the desorption mode;
    a second gas valve (29) connected between the gas tank (33) and the first and second gas inlets (23,24), the second valve (29) being closed when the device operates in the desorption mode and open when the device operates in the adsorption mode;
    a third gas valve (27) connected between the second valve (29) and the first gas inlet (23), the third gas valve being closed when the device operates in the desorption mode and open when the device operates in the adsorption mode;
    whereby the first gas valve (25), the second gas valve (29) and the third gas valve (27) are arranged such that, in the adsorption mode, the gas tank (33) is in communication with the second inner part (36) of the injector (1) through the second gas inlet (24) and with the first inner part (35) of the injector through the second gas inlet (23), whereas, in the desorption mode, the gas tank (33) is in communication with only the second inner part (36) of the injector (1) through the second gas inlet (24).

4. A device according to claim 1, wherein the hydraulic system for gases further comprises a first pressure reducer (26) connected between the gas tank (33) and the second gas inlet (24), for regulating, in the desorption mode, pressure of the pressurized gas flow but not the pressurized gas flow entering the injector (1) through the first gas inlet (23) in the adsorption mode.

5. A device according to claim 1, wherein the modified hydraulic system for gases further comprises a second pressure reducer (31) connected between the gas tank (33) and the first and second gas inlets (23,24), for specifically regulating pressure of the pressurized gas flowing entering the injector (1) through the first and second gas inlets (23,24) in the adsorption mode, but not in the desorption mode.

6. A device according to claim 1, wherein the modified hydraulic system for gases further comprises a third pressure reducer (32) connected between the gas tank (33) and the first and second gas inlets (23,24), for generally regulating pressure of the pressurized gas flowing entering the injector (1) through the first and second gas inlets (23,24), in the desorption mode and in the adsorption mode.

7. A device according to claim 1, wherein the modified hydraulic system for gases further comprises a first regulator valve (28) connected between the gas tank (33) and the first gas inlet (23), for regulating the pressurized gas flowing entering the injector (1) through the first gas inlet (23) in the adsorption mode, but not for regulating the pressurized gas flow entering the injector (1) through the second gas inlet (24) in the desorption mode.

8. A device according to claim 1, wherein the modified hydraulic system for gases further comprises a second regulator valve (30) connected between the gas tank (33) and the second gas inlet (24), for regulating the pressurized gas flow entering the injector (1) through the second gas inlet (24) in the adsorption mode, but not for regulating the pressurized gas flow entering the injector (1) through the second gas inlet (24) in the desorption mode.

9. A device according to claim 1, wherein the outlet system further comprises a flow regulator valve (18) connected to the second tube (16), for regulating the pressurized gas flow within the glass liner (2).

10. A device according to claim 1, wherein the outlet system further comprises a pressure reducer (18) connected to the second tube (16), for regulating the pressurized gas flow within the glass liner (2).

11. A device according to claim 1, wherein the outlet system further comprises a vacuum system connected to the second tube (16), for regulating the pressurized gas flow within the glass liner (2).

12. A device according to claim 1, wherein the second tube (16) is connected to a further waste (20).

* * * * *